US008003827B2

(12) United States Patent
Nelson et al.

(10) Patent No.: US 8,003,827 B2
(45) Date of Patent: Aug. 23, 2011

(54) METHOD FOR PRODUCING PHENOL AND ACETONE

(75) Inventors: Mark E. Nelson, Mount Vernon, IN (US); Arkady Samuilovich Dykman, St. Petersburg (RU); Andrey Vladimirovich Zinenkov, St. Petersburg (RU); Victor Vladimirovich Pinson, St. Petersburg (RU); Ilja Nikolayevich Grebenshchikov, St. Petersburg (RU)

(73) Assignee: Sabic Innovative Plastics IP B.V. (NL)

( * ) Notice: Subject to any disclaimer, the term of this patent is extended or adjusted under 35 U.S.C. 154(b) by 0 days.

(21) Appl. No.: 12/424,447

(22) Filed: Apr. 15, 2009

(65) Prior Publication Data
US 2009/0264685 A1 Oct. 22, 2009

(30) Foreign Application Priority Data

Apr. 16, 2008 (RU) .................................. 2008115046

(51) Int. Cl.
*C07C 45/53* (2006.01)
*C07C 37/08* (2006.01)
(52) U.S. Cl. ........................................ 568/398; 568/798
(58) Field of Classification Search .................. 568/398, 568/798
See application file for complete search history.

(56) References Cited

U.S. PATENT DOCUMENTS

| 3,271,457 | A | 9/1966 | Bewley et al. |
| 4,246,203 | A | 1/1981 | Wirth |
| 6,057,483 | A | 5/2000 | Zakoshansky et al. |
| 7,109,385 | B2 | 9/2006 | Tatake et al. |
| 7,482,493 | B2 | 1/2009 | Nelson et al. |
| 7,485,758 | B2 | 2/2009 | Nelson et al. |
| 2005/0222466 | A1 | 10/2005 | Tatake et al. |

FOREIGN PATENT DOCUMENTS

| GB | 721700 A | 1/1955 |
| RU | 2068404 C1 | 10/1996 |
| RU | 2121477 C1 | 11/1998 |
| RU | 2291852 C1 | 1/2007 |
| WO | WO2005/097720 A1 | 10/2005 |

OTHER PUBLICATIONS

PCT International Search Report for International Patent Application No. PCT/US2009/040804.
Zakoshansky, V.M. Scientific Publication, Conference Materials, Development Prospects for Chemical Processing of Fossil Fuel. "Cumene Process of Phenol-Acetone Production—History and Evolution". Khimizdata, St. Petersburg, RU pp. 25-39, 2005.
Zakoshansky, V.M. "Direction for the Development of Phenolic Process—Safety, Selectivity and Quality of the Products: I. Cumene Oxidation into Cumene Hydroperoxide (CHP)". ISBN 5-901065-94-8. Process of Oil Refining and Petrochemistry. SP6., 2005. pp. 89-107.
Zakoshansky, V.M. "Direction for Phenol Process Development—Security, Selectivity Quality and Marketable Product: II. Decomposition of Technical Cumyl Hydroperioxide". ISBN 5-901065-94-8. Process of Oil Refining and Petrochemistry. SP6., 2005. pp. 108-130.
Vasileva, I.I. and Zakoshansky, V.M. "Direction of Development Phenolic Process—Safety, Selectivity and Quality of the Commodity Products: III. Technologies of Separation and Quality of Products". ISBN 5-901065-94-8. Process of Oil Refining and Petrochemistry. SP6., 2005. pp. 131-154.
Kirk-Othmer Encyclopedia of Chemical Technology. Fourth Edition, vol. 18. Phenol. pp. 592-602.

*Primary Examiner* — Sikarl Witherspoon
(74) *Attorney, Agent, or Firm* — Cantor Colburn LLP

(57) ABSTRACT

A method for producing phenol and acetone in a multi-stage process at an elevated temperature from a cumene hydroperoxide mixture comprising cumene, comprises the steps of:
  a) distilling an amount of cumene from the cumene hydroperoxide mixture until the cumene mass % is 0 to 7 mass % relative to the total mass of the cumene hydroperoxide mixture,
  b) reacting the cumene hydroperoxide mixture with an acid catalyst form to a second mixture comprising phenol, acetone and dicumyl peroxide in a first stage, and
  c) decomposing the second mixture in a second stage to produce phenol and acetone,
wherein an amount of phenol approximately equal to the amount of distilled from the cumene hydroperoxide mixture is added to the cumene hydroperoxide mixture before the reacting step b). The amount of hydroxyacetone is reduced, thereby, improving the quality of commercial-grade phenol and the products made from the phenol.

15 Claims, 1 Drawing Sheet

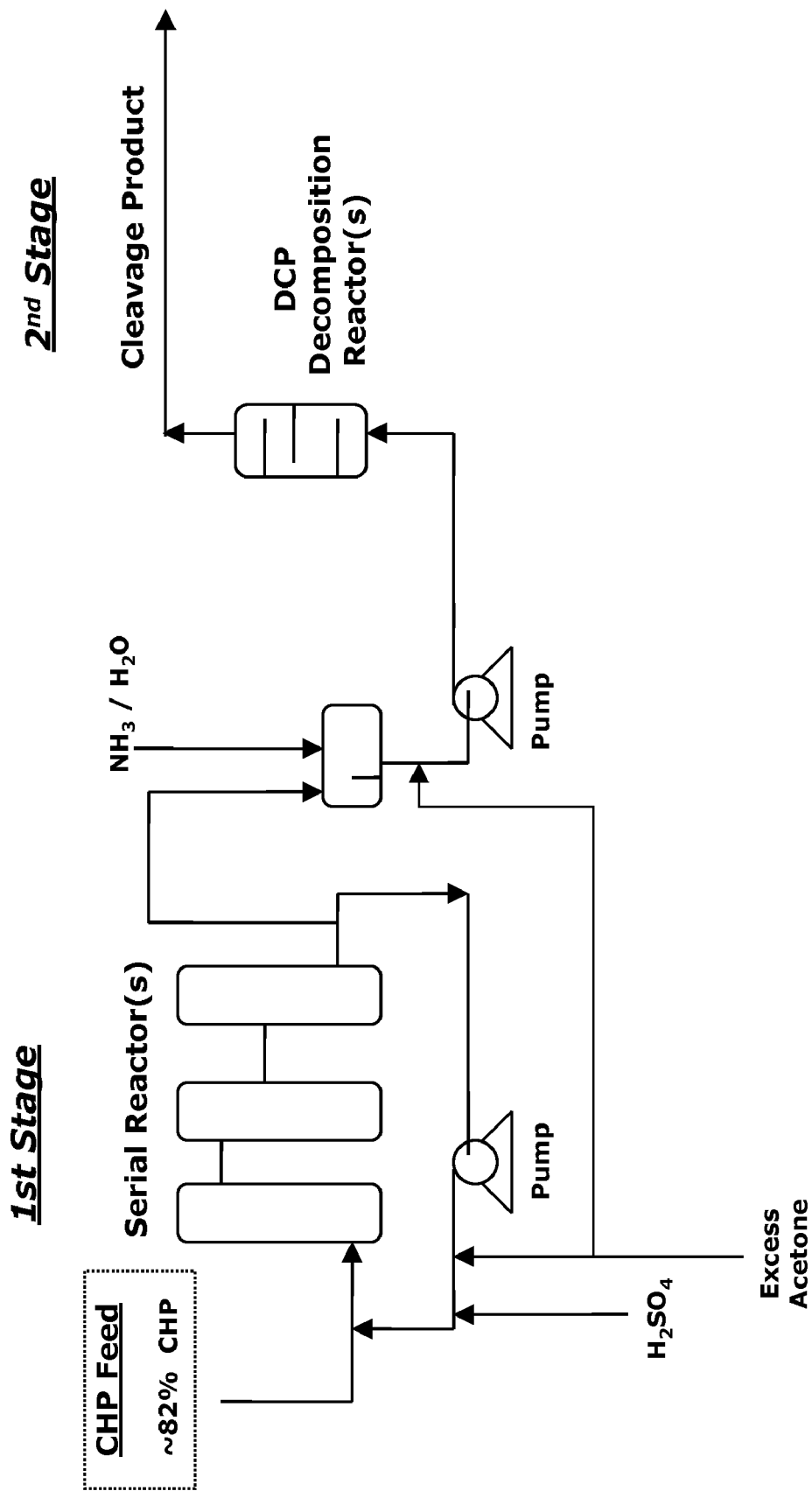

METHOD FOR PRODUCING PHENOL AND ACETONE

CROSS REFERENCE TO RELATED APPLICATIONS

This application claims priority to Russian Application Serial No. 2008115046, filed Apr. 16, 2008. This disclosure is hereby fully incorporated herein by reference.

BACKGROUND

The present invention relates to the field of industrial organic synthesis, particularly to the production of phenol and acetone by the cumene method.

A well-known method for producing phenol and acetone by the oxidation of cumene with atmospheric oxygen, followed by the acid-catalyzed decomposition of cumene hydroperoxide, makes it possible to obtain both target products (phenol and acetone) at a high yield (Khruzhalov B. D., Golovanenko B. N., Co-production of phenol and acetone, Moscow, GosKhimIzdat, 1964). However, the yield of heavy byproducts, so-called "phenol resins," of this process remains considerable.

There are known methods of producing phenol and acetone in which, in order to reduce the yield of phenol resins (also referred to as "heavies"), cumene oxidation products containing cumene hydroperoxide (CHP), cumene, and dimethylphenylcarbinol (DMPC, also referred to as dimethylbenzyl alcohol (DMBA)) are cleaved in two stages in the presence of sulfuric acid. The first stage involves decomposition of most (97 to 99%) of the CHP and synthesis of dicumyl peroxide (DCP) from DMPC and CHP at 55 to 80° C. The second stage involves adding acetone to the resulting reaction mixture containing phenol, acetone, DMPC, and DCP at a temperature of 80 to 120° C. The acetone is added in an amount equal to 1.5 to 1.8 times its initial concentration. This process is accompanied by the cleavage of the DCP formed in the first stage, decomposition of the residual CHP, and dehydration of a portion of the residual DMPC (Russian patent Nos. 2,068,404 and 2,121,477).

The aforementioned methods make it possible to markedly reduce the amount of byproducts in comparison with the one-stage decomposition processes (resin yield: 25 kg/t of phenol). At the same time, the amount of the hydroxyacetone (HA) byproduct remains high in these improved two stage processes (for example, more than 1000 ppm).

Hydroxyacetone is a source of 2-methylbenzofuran, which is difficult to separate from phenol and which has an adverse effect on the color indexes of products made from impure commercial-grade phenol. Hydroxyacetone can be removed from phenol, for example, by an alkaline treatment, but this makes the technology of the process more complicated (Vasilieva I. I., Zakhoshansky V. M., Collection of articles titled "Petrochemical and Oil Refining Processes," SPb, Giord, 2005, p. 344).

A method is known for decomposing technical-grade CHP in a medium composed of reaction products containing up to 13 mass % of cumene at a phenol/acetone molar ratio of greater than 1 and a sulfuric acid concentration of 0.003 to 0.015 mass % (Russian Patent No. 2,291,852). The decomposition process is carried out in two stages. In the first stage, technical-grade CHP is decomposed in at least two serially connected reactors while the reaction mass is circulated at 40 to 65° C. in the presence of the sulfuric acid catalyst having a concentration of 0.003 to 0.015 mass % in the reaction mass (depending on the temperature in the reactors and the phenol/acetone ratio). The volume in which the raw material (CHP) is introduced should not be more than 10%, and in embodiments is preferably less than 5%, of the circulation volume of the reaction mass, while the circulation factor (ratio of the flow rate of the circulating mass to the flow rate of the technical-grade CHP fed as a raw material) is from 8 to 50. If the CHP conversion is equal to 95 to 99.8% under these conditions, the CHP decomposes to give phenol and acetone, and DCP is synthesized from CHP and DMPC.

In the second stage, the synthesized DCP and the residual CHP are decomposed in the final reactor at a temperature of 90 to 140° C. while half of the added sulfuric acid is first neutralized with ammonia. The hydroxyacetone yield decreases from a level of greater than 0.1 mass % (1000 parts per million (ppm)) to 0.04 mass % (400 ppm, as mentioned in Russian Patent No. 2,291,852). However, application of this method is premised on the use of phenol that has been purified in a phenol purification system, and the purification of phenol involves additional manufacturing steps and power consumption.

Another method of CHP decomposition is a method that is carried out in two stages according to Russian Patent No. 2,142,932. This CHP decomposition process is carried out in three serially arranged mixing reactors in the first stage, and a displacement reactor in the second stage. The CHP is decomposed in the first stage under conditions close to isothermal (that is, at a temperature of 47 to 50° C. and a concentration of 0.018 to 0.020 mass % for the sulfuric acid catalyst), while the reaction mass is additionally diluted with acetone in an amount equal to 5 to 8 mass % relative to the amount of CHP supplied. Almost all of the CHP reacts in the process, and DCP forms from part of the CHP and DMPC.

The process in the second stage is carried out while the sulfuric acid is partially neutralized with ammonia to form ammonium hydrosulfate at 120 to 140° C., and while some water is added. The concentration of acid is 0.009 to 0.010 mass %. The CHP and DCP are decomposed in a reaction medium containing phenol and acetone, both of which have formed from the CHP. Additional acetone may optionally be added to the reactor if desired.

A disadvantage of the prior-art method is the presence of hydroxyacetone in the resulting phenol. The presence of hydroxyacetone has an adverse effect on the phenol quality. There is a need for a method to further reduce the amount of hydroxyacetone in the resulting phenol produced.

SUMMARY OF THE INVENTION

Some or all of the above-described deficiencies are addressed by a method for producing phenol and acetone in a multi-stage process at an elevated temperature from a cumene hydroperoxide mixture comprising cumene, the method comprising the steps of:

a) distilling an amount of cumene from the cumene hydroperoxide mixture until the cumene mass % is 0 to 7 mass % relative to the total mass of the cumene hydroperoxide mixture, b) reacting the cumene hydroperoxide mixture with an acid catalyst form to a second mixture comprising phenol, acetone and dicumyl peroxide in a first stage, and c) decomposing the second mixture in a second stage to produce phenol and acetone, wherein an amount of phenol approximately equal to the amount of distilled from the cumene hydroperoxide mixture is added to the cumene hydroperoxide mixture before the reacting step b).

In another embodiment, a method for producing phenol and acetone from a cumene hydroperoxide mixture in a multi-stage process at an elevated temperature, comprises the steps of:
  a) adding an amount of phenol to the cumene hydroperoxide mixture and distilling the cumene from the cumene hydroperoxide mixture until the cumene mass % is 0 to 7 mass % relative to the total mass of the cumene hydroperoxide mixture,
  b) reacting the cumene hydroperoxide mixture with an acid catalyst to form a second mixture comprising dicumyl peroxide in a first stage, and
  c) decomposing the second mixture in a second stage to produce phenol and acetone.

In another embodiment, a method for producing phenol and acetone from a cumene hydroperoxide mixture in a multi-stage process at an elevated temperature, comprises the steps of:
  a) distilling an amount of cumene from the cumene hydroperoxide mixture,
  b) reacting the cumene hydroperoxide mixture with an acid catalyst to form a second mixture comprising dicumyl peroxide in a first stage, and
  c) decomposing the second mixture in a second stage to produce a third mixture comprising phenol, acetone, and hydroxyacetone,
wherein an amount of phenol approximately equal to the amount of cumene distilled from the cumene hydroperoxide mixture is added to the cumene hydroperoxide mixture before the reacting step b),
and wherein the amount of hydroxyacetone in the third mixture is less than or equal to 300 ppm.

BRIEF DESCRIPTION OF THE DRAWING

The FIGURE is a process flow diagram of an embodiment of the two-stage cleavage process of the invention.

DETAILED DESCRIPTION OF THE INVENTION

The inventors have found a way to further reduce the amount of hydroxyacetone in the decomposition products (phenol and acetone) of technical-grade CHP by adding an amount of phenol to the reaction prior to the decomposition step. The CHP concentration remains unchanged in the process, and the level or amount of hydroxyacetone in the decomposition products is reduced. This process forms CHP having a low level (less than 7.0 mass % residual cumene), which is then decomposed in a second step.

In embodiments, the reacting in the first stage is at a temperature of from 47 to 50° C., and the decomposing in the second stage is at a temperature of from 120 to 140° C.

As used herein, technical-grade cumene hydroperoxide (CHP) refers to CHP having a CHP concentration of from about 50 to 92 mass %, specifically from about 65 to 85 mass %, more specifically from 80 to 84 mass %. The actual CHP concentration is not critical, as long as the amount of cumene can be reduced to less than 7 mass % prior to the decomposition step.

The phenol can be added to the CHP mixture prior to the step of distilling the cumene from the cumene hydroperoxide mixture, during the distilling step, or after the distilling step, as long as it is added before the decomposition step. In an embodiment, the phenol is added to the CHP mixture just prior to the distilling step to facilitate cumene removal.

The low-cumene containing CHP resulting mixture is decomposed in two stages. The raw material (technical-grade CHP) is diluted in the first stage with acetone in an amount equal to 5 to 8 mass % relative to the amount of the supplied CHP, at a temperature of 47 to 50° C. and a sulfuric acid concentration of 0.007 to 0.018 mass %. The volume in which the raw material CHP is fed must not exceed 10% of the volume of the circulating reaction mass while the circulation factor (ratio of the flow rate of the circulating mass to the flow rate of the raw material being fed) is kept at 8 to 50. Under these conditions, CHP decomposes to form phenol and acetone, and DCP is synthesized from CHP and DMPC, at a CHP conversion rate of 95 to 99.8%. An aqueous ammonia solution is added to the resulting reaction mass in an amount necessary to neutralize approximately half of the supplied sulfuric acid. Acetone is also added in an amount of 50 to 80 mass % relative to the acetone content of the reaction mixture. The partially neutralized and diluted reaction mass is fed to the second-stage reactor, where the remaining DCP is decomposed at 120 to 140° C.

While sulfuric acid is used as the catalyst in an embodiment, other catalysts may also be used. Examples of other catalysts include: hydroxy aromatic sulfonic acids or mixtures of hydroxy aromatic sulfonic acids. The hydroxy aromatic sulfonic acids may be made by, for example, a reaction of a phenol or para-cumyl phenol, with sulfuric acid (see, for example, U.S. Pat. Nos. 7,485,758 and 7,482,493). In an embodiment, the sulfuric acid used is a sulfuric acid solution comprising at least 75 wt. % sulfuric acid, specifically at least 90 wt. %, more specifically at least 90 to 95 wt. % sulfuric acid.

CHP oxidate formed in the cumene oxidation reactors has a concentration of about 15 to 30 mass % CHP. By distillation (or stripping/concentrating), this mixture is concentrated by cumene removal to form technical-grade CHP having between 50 and 92 mass % CHP. It is important to maintain the cumene level in the technical-grade CHP at an optimum level, as low as possible or practical. In an embodiment, the cumene level is maintained at a level of from 0 to no more than 7.0 mass %. As required, this is accomplished by the addition of phenol in the distillation process and then removing additional cumene to the desired level. The amount of phenol added is approximately equal to the amount of cumene to be removed from the starting technical-grade CHP. The cumene level is maintained as low as possible. One skilled in the art will recognize that the lower the cumene level, the lower the resulting hydroxyacetone levels that can be achieved, but levels less than about 5 mass % cumene are not as practical on a commercial scale.

Using technical-grade CHP, where the cumene level has been reduced to the desired level, for example, no more than 7.0 mass % cumene by distillation (stripping), it is possible to significantly reduce the hydroxyacetone yield, for example, from 0.12 to 0.03 or even 0.02 mass % (from about 1200 ppm to about 300 ppm, or even 200 ppm), compared to methods where technical-grade CHP having higher levels (such as more than 12 mass %) of cumene is used the feed material to first stage cleavage. Reducing the level of hydroxyacetone has a marked effect on the quality of commercial-grade phenol, particularly the color of products made from the resulting phenol, such as bisphenol A and polycarbonate.

Concentration by distillation of the CHP oxidate from cumene oxidation reactors becomes more difficult as the mass % CHP increases due to safety concerns. To facilitate the safe concentration of CHP while reducing the residual cumene content to no more than 7.0 mass % cumene, phenol may be added prior to the final concentration step. Alternatively, phenol may be added after the residual cumene content has been reduced to no more than 7.0 mass %. Phenol substitution for cumene allows for lower reboiler temperatures and increased safety. The phenol is added prior to cleavage (decomposition step), but it is not critical when it is added and may be added at different times, as desired, as long as it has been added before cleavage (decomposition). In some embodiments, it is desired to add the phenol in the last concentration step. The amount of phenol added is approximately equal to the amount of cumene to be removed from the starting technical-grade CHP. For example, if about 6 mass % cumene is to be removed from CHP having a starting cumene level of about 13 mass %, therefore bringing the cumene level to about 7 mass %, then about 6 mass % phenol is added.

The FIGURE shows a process flow diagram of an embodiment of a typical two-stage CHP decomposition/cleavage process. In the first step, the raw material CHP (technical-grade CHP having a CHP level of from about 50 to 92 mass %) is fed to a first-stage reactor. In an embodiment, the first-stage reactor is a series of serially connected reactors, such as at least two serially connected reactors, specifically at least three serially connected reactors, although a single reactor may also be used. Efficiency and heat transfer is improved with multiple reactors serially connected. Excess acetone and catalyst (such as sulfuric acid) are fed to the reactors. The CHP is diluted with the excess acetone in an amount equal to 5 to 8 mass % relative to the amount of the CHP in the feed stream. The stream is fed through the one or more reactors, and the catalyst is also fed into the stream to form the reaction mass. An aqueous ammonia solution is added to the resulting reaction mass to neutralize half of the supplied sulfuric acid. The partially neutralized and diluted reaction mass is fed to the second-stage reactor or reactors, where the remaining DCP is decomposed. In an embodiment, one reactor is used in the second stage, although more than one may be used if desired.

The method is illustrated by the following non-limiting examples.

EXAMPLES

Comparative Example (CEx)

A raw material for decomposition was prepared using technical-grade CHP by adding 21.7 g of acetone and 1.2 g of water to 250 g of the technical-grade CHP (having the composition shown in Table 1) form a mixture. The resulting mixture was used as a starting material to obtain phenol and acetone by CHP decomposition.

CHP was decomposed in a pilot unit composed of two reactors: a first-stage reactor having a volume of 12 mL, and a second-stage displacement reactor having a volume of 7 mL. The reaction mass from the first-stage reactor was partially fed to the second reactor and was partially returned to the inlet of the first reactor, whereby the reaction mass was circulated. The feed rate of the raw material (CHP) was 30 mL/h. Sulfuric acid was fed as a catalyst into the first reactor such that the sulfuric acid concentration in the reaction mass was maintained at about 180 to 200 ppm of sulfuric acid on average. The circulation rate of the reaction mass was 500 mL/h. The reactor jacket was heated in order to maintain the temperature at 47 to 50° C. The stream exiting the first-stage reactor was fed to an intermediate vessel having a capacity of 5 mL, and a 1.64% ammonia solution and acetone were fed to the vessel at the rates of 25 μL/h and 8 mL/h, respectively, to partially neutralize and dilute the reaction mass, such that approximately half of the sulfuric acid is neutralized. The partially neutralized and diluted reaction mass was fed to the second-stage reactor, which was heated to a temperature of 140° C. The stream exiting the second-stage reactor was cooled to room temperature, neutralized with sodium hydrocarbonate, and analyzed by gas liquid chromatography. The hydroxyacetone content of the reaction mass was 0.12 mass % (1200 ppm).

Example 1 (Ex1)

33 g of phenol was added to 250 g of technical-grade CHP having the composition shown in Table 1 to form a mixture. Cumene was distilled off from the resulting mixture at a residual pressure of 4 to 6 mm Hg. A fraction having a boiling point of 40 to 60° C. and containing 99.04% of cumene, 0.9% of phenol, and 0.06% of methylstyrene (as indicated by the results of gas liquid chromatography) was obtained as a distillate in an amount of 33.5 g. The composition of the bottom product is shown in Table 2. To the resulting bottom product, 21.7 g of acetone and 1.2 g of water were added to form a mixture. The resulting mixture, which contained 0.88 mass % cumene, was used as a starting material to obtain phenol and acetone by CHP decomposition.

CHP was decomposed in a pilot unit composed of two reactors: a first-stage reactor having a volume of 12 mL, and a second-stage displacement reactor having a volume of 7 mL. The reaction mass from the first-stage reactor was partially fed to the second reactor and was partially returned to the inlet of the first reactor, whereby the reaction mass was circulated. The feed rate of the raw material (CHP) was 30 mL/h. Sulfuric acid was fed as a catalyst into the first reactor such that the sulfuric acid concentration in the reaction mass was maintained at about 70 ppm of sulfuric acid on average (sulfuric acid having a concentration of 0.007 mass %). The circulation rate of the reaction mass was 500 mL/h. The reactor jacket was heated in order to maintain the temperature at 47 to 50° C. The stream exiting the first-stage reactor was fed to an intermediate vessel having a capacity of 5 mL, and a 1.64% ammonia solution and acetone were fed to the vessel at the rates of 10 μL/h and 8 mL/h, respectively, to partially neutralize and dilute the reaction mass, such that approximately half of the sulfuric acid is neutralized. The partially neutralized and diluted reaction mass was fed to the second-stage reactor, which was heated to a temperature of 140° C. The stream exiting the second-stage reactor was cooled to room temperature, neutralized with sodium hydrocarbonate, and analyzed by gas liquid chromatography. The hydroxyacetone content of the reaction mass was 0.02 mass % (200 ppm).

TABLE 1

Composition of the starting technical-grade CHP

| Component | Composition, mass % |
|---|---|
| Cumene hydroperoxide | 79.23 |
| Cumene | 12.86 |
| Phenol | 0.08 |

TABLE 1-continued

Composition of the starting technical-grade CHP

| Component | Composition, mass % |
|---|---|
| α-Methylstyrene | 0.05 |
| Acetophenone | 1.14 |
| Dimethyl phenyl carbinol | 5.21 |
| Dicumyl peroxide | 0.77 |
| Unidentified products | 0.66 |

TABLE 2

Composition of bottom product of Example 1 after adding phenol and distilling off cumene

| Component | Composition, mass % |
|---|---|
| Cumene hydroperoxide | 78.36 |
| Cumene | 0.88 |
| Phenol | 13.1 |
| α-Methylstyrene | 0.08 |
| Acetophenone | 0.99 |
| Dimethyl phenyl carbinol | 5.06 |
| Dicumyl peroxide | 0.78 |
| Unidentified products | 0.75 |

Example 2 (Ex2)

In this example, only half as much phenol was added to the technical-grade CHP. 16.5 g of phenol was added to 250 g of technical-grade CHP (having the composition shown in Table 1). Residual cumene was removed using the same process as described in Example 1. As a result, a bottom product having the composition shown in Table 3 was obtained (which contained 6.87 mass % cumene).

Acetone was added to the resulting bottom product in the same amounts as in Example 1, and decomposition was carried out under the conditions described in Example 1. The hydroxyacetone content of the resulting decomposition mass was 0.03 mass % (300 ppm).

TABLE 3

Composition of bottom product of Example 2 after adding phenol and distilling cumene

| Component | Composition, mass % |
|---|---|
| Cumene hydroperoxide | 78.8 |
| Cumene | 6.87 |
| Phenol | 6.59 |
| α-Methylstyrene | 0.06 |
| Acetophenone | 1.06 |
| Dimethyl phenyl carbinol | 5.13 |
| Dicumyl peroxide | 0.78 |
| Unidentified products | 0.70 |

The Examples and Tables show that when cumene is first removed from technical-grade CHP before cleavage (using the two-step process) into phenol and acetone, there was a significant reduction of hydroxyacetone yield. In the Comparative Example, no phenol was added to the starting raw material (technical-grade CHP), while in Examples 1 and 2, phenol was added (33 g in Example 1, and 16.5 g in Example 2, to 250 g of CHP starting material, with a cumene content of 32.2 g). The addition of the phenol significantly reduced the level of hydroxyacetone in the final product, as shown in Table 4. Although twice as much phenol was added in Example 1 compared to Example 2, the reduction in the level of hydroxyacetone was much less than the reduction seen from the Comparative Example to Example 2.

TABLE 4

Yield of Hydroxyacetone (when comparing added phenol).

| | Cumene (g) | Phenol (g) | Mass % Hydroxyacetone | ppm Hydroxyacetone |
|---|---|---|---|---|
| CEx | 32.2 | 0 | 0.12 | 1200 |
| Ex2 | 32.2 | 16.5 | 0.03 | 300 |
| Ex1 | 32.2 | 33.0 | 0.02 | 200 |

The Examples were performed in at laboratory scale, but they are intended to represent a plant setting with varying configurations and numbers of reactors. Examples of varying configurations may include, but are not limited to, a cumene stripping operation, varying number of columns used for distillation, such as a single reactor or multiple columns in series, oxidation of cumene to form CHP prior to distillation, and the like. One skilled in the art will appreciate the varying configurations that may be used to achieve the same outcome.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims. One skilled in the art would recognize that in a reaction conducted using a feedstock of a different composition than the starting composition used in the experiments, the results may differ from those given in the Examples of the present invention, but the positive effect of using this invention would be retained.

The invention claimed is:

1. A method for producing phenol and acetone in a multi-stage process at an elevated temperature from a cumene hydroperoxide mixture comprising cumene, the method comprising the steps of:
   a) distilling an amount of cumene from the cumene hydroperoxide mixture until the cumene mass % is 0 to 7 mass % relative to the total mass of the cumene hydroperoxide mixture,
   b) reacting the cumene hydroperoxide mixture with an acid catalyst form to a second mixture comprising phenol, acetone and dicumyl peroxide in a first stage, and
   c) decomposing the second mixture in a second stage to produce phenol and acetone,
   wherein an amount of phenol, approximately equal to the amount of cumene distilled from the cumene hydroperoxide mixture, is added to the cumene hydroperoxide mixture before the reacting step b).

2. The method of claim 1, wherein the reacting in the first stage is at a temperature of from 47 to 50° C., and the decomposing in the second stage is at a temperature of from 120 to 140° C.

3. The method of claim 1, wherein the acid catalyst is sulfuric acid.

4. The method of claim 1, wherein the cumene hydroperoxide mixture comprises between 50 mass % and 92 mass % cumene hydroperoxide relative to the total mass of the cumene hydroperoxide mixture.

5. The method of claim 1, wherein the cumene hydroperoxide mixture comprises between 65 mass % and 85 mass % cumene hydroperoxide relative to the total mass of the cumene hydroperoxide mixture.

6. The method of claim 1, wherein the cumene hydroperoxide mixture comprises between 80 mass % and 84 mass % cumene hydroperoxide relative to the total mass of the cumene hydroperoxide mixture.

7. The method of claim 1, wherein the step of reacting the cumene hydroperoxide is in at least two serially connected reactors.

8. A method for producing phenol and acetone from a cumene hydroperoxide mixture in a multi-stage process at an elevated temperature, the method comprising the steps of:
   a) adding an amount of phenol to the cumene hydroperoxide mixture and distilling the cumene from the cumene hydroperoxide mixture until the cumene mass % is 0 to 7 mass % relative to the total mass of the cumene hydroperoxide mixture,
   b) reacting the cumene hydroperoxide mixture with an acid catalyst to form a second mixture comprising dicumyl peroxide in a first stage, and
   c) decomposing the second mixture in a second stage to produce phenol and acetone.

9. The method of claim 8, wherein the reacting in the first stage is at a temperature of from 47 to 50° C., and the decomposing in the second stage is at a temperature of from 120 to 140° C.

10. The method of claim 8, wherein the acid catalyst is sulfuric acid.

11. The method of claim 8, wherein the step of reacting the cumene hydroperoxide is in at least two serially connected reactors.

12. A method for producing phenol and acetone in a multi-stage process at an elevated temperature from a cumene hydroperoxide mixture comprising cumene, the method comprising the steps of:
   a) distilling an amount of cumene from the cumene hydroperoxide mixture,
   b) reacting the cumene hydroperoxide mixture with an acid catalyst to form a second mixture comprising dicumyl peroxide in a first stage, and
   c) decomposing the second mixture in a second stage to produce a third mixture comprising phenol, acetone, and hydroxyacetone,
   wherein an amount of phenol approximately equal to the amount of cumene distilled from the cumene hydroperoxide mixture is added to the cumene hydroperoxide mixture before the reacting step b),
   and wherein the amount of hydroxyacetone in the third mixture is less than or equal to 300 ppm.

13. The method of claim 12, wherein the reacting in the first stage is at a temperature of from 47 to 50° C., and the decomposing in the second stage is at a temperature of from 120 to 140° C.

14. The method of claim 12, wherein the amount of hydroxyacetone in the third mixture is less than or equal to 200 ppm.

15. The method of claim 12, wherein the cumene mass % in the cumene hydroperoxide is reduced in the distilling step to 0 to 7 mass % relative to the total mass of the cumene hydroperoxide mixture.

\* \* \* \* \*